United States Patent
Eh et al.

(10) Patent No.: US 11,066,625 B2
(45) Date of Patent: Jul. 20, 2021

(54) BLENDS CONTAINING ENANTIOMERICALLY PURE AMBROCENIDE®

(71) Applicant: SYMRISE AG, Holzminden (DE)

(72) Inventors: Marcus Eh, Holzminden (DE); Stefan Lambrecht, Hehlen (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 16/639,146

(22) PCT Filed: Aug. 25, 2017

(86) PCT No.: PCT/EP2017/071424
§ 371 (c)(1),
(2) Date: Feb. 14, 2020

(87) PCT Pub. No.: WO2017/186973
PCT Pub. Date: Nov. 2, 2017

(65) Prior Publication Data
US 2020/0172830 A1   Jun. 4, 2020

(51) Int. Cl.
| | | |
|---|---|---|
| C11B 9/00 | (2006.01) |
| A61K 8/49 | (2006.01) |
| A61Q 5/02 | (2006.01) |
| A61Q 13/00 | (2006.01) |
| C07C 33/16 | (2006.01) |
| C07C 35/37 | (2006.01) |
| C07C 43/162 | (2006.01) |
| C07C 49/547 | (2006.01) |
| C07D 317/70 | (2006.01) |

(52) U.S. Cl.
CPC .......... *C11B 9/0076* (2013.01); *A61K 8/4973* (2013.01); *A61Q 5/02* (2013.01); *A61Q 13/00* (2013.01); *C07C 33/16* (2013.01); *C07C 35/37* (2013.01); *C07C 43/162* (2013.01); *C07C 49/547* (2013.01); *C07D 317/70* (2013.01)

(58) Field of Classification Search
CPC ..... A61K 8/498; C07D 317/70; C11B 9/0076
See application file for complete search history.

(56) References Cited

U.S. PATENT DOCUMENTS

2012/0077722 A1* 3/2012 Dilk ............... A61K 8/4973
                                                           510/103
2017/0114299 A1* 4/2017 Schatkowski ........ C11B 9/0076

FOREIGN PATENT DOCUMENTS

| EP | 1634864 A2 | 3/2006 |
| EP | 1947166 A1 | 7/2008 |
| EP | 2947078 A1 | 11/2015 |

OTHER PUBLICATIONS

International Search Report and Written Opinion dated Oct. 20, 2017 for corresponding PCT Application No. PCT/EP2017/071424.
Pantent, J. et al.; "New woody and ambery notes from cedarwood and turpentine oil", Chemistry and Biodiversity, Helvetica Chimica Acta, vol. 1, No. 12, 2004, pp. 1936-1948 XP002543298.
CH Office Action and Examiner's Comments dated Dec. 6, 2019 for corresponding CH Application No. 1334/19.

* cited by examiner

*Primary Examiner* — John R Hardee
(74) *Attorney, Agent, or Firm* — Polsinelli PC

(57) ABSTRACT

The present invention relates in particular to a mixture comprising the compound of formula (Ia) as described herein, wherein the mixture is free or essentially free of the compound of formula (Ib) as described herein, preferably of the compounds of formulae (Ib) and furthermore (Ic) and/or (Id) as described herein. The invention further relates to a method for manufacturing said mixture, fragrance substance compositions containing or consisting of said mixture, perfumed products containing said mixtures or fragrance substance compositions, and various methods and uses for imparting, modifying and/or enhancing certain odour notes.

12 Claims, No Drawings

BLENDS CONTAINING ENANTIOMERICALLY PURE AMBROCENIDE®

CROSS-REFERENCE TO RELATED APPLICATIONS

This application is a national stage application (under 35 U.S.C. § 371) of PCT/EP2017/071424, filed Aug. 25, 2017, which is incorporated herein by reference in its entirety.

The present invention primarily relates to a mixture comprising the compound of formula (Ia) as described herein, wherein the mixture is free or essentially free of the compound of formula (Ib) as described herein, preferably of the compounds of formulae (Ib) and furthermore (Ic) and/or (Id) as described herein. The invention further relates to a method for manufacturing said mixture, fragrance substance compositions containing or consisting of said mixture, perfumed products containing said mixtures or fragrance substance compositions, and various methods and uses for imparting, modifying and/or enhancing certain odour notes.

Further aspects and preferred embodiments of the present invention result from the following explanations, the attached examples and, in particular, the attached patent claims.

Ambrocenide® has the following chemical structure:

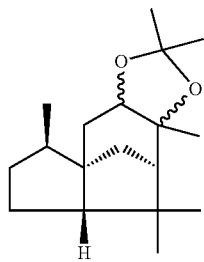

(I)

The wavy lines thereby can mean alpha- or beta-configuration independently of each other. Accordingly, Ambrocenide® can generally comprise one, two, three or all of the following stereoisomers:

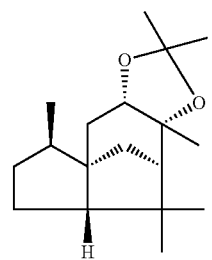

(Ia)

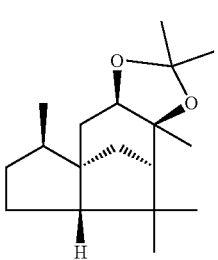

(Ib)

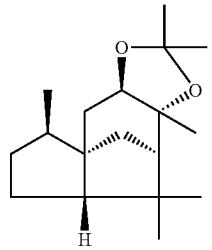

(Ic)

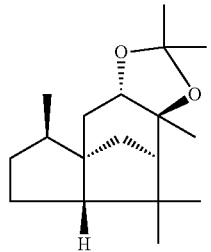

(Id)

One possibility for manufacturing Ambrocenide® is disclosed in EP 0 857 723 B1. First, (−)-alpha-cedrene (1) is converted to (−)-alpha cedrene epoxide (2) by treatment with peracetic acid. The epoxide obtained (2) is then converted into a mixture of the epimeric cedrane diols (3) by acid catalysed ring opening. Ambrocenide® ((4) with R═R'═CH$_3$: Compound of the formula (I)) can then be obtained from the diols (3) by conversion with dimethoxypropane under acid catalysis:

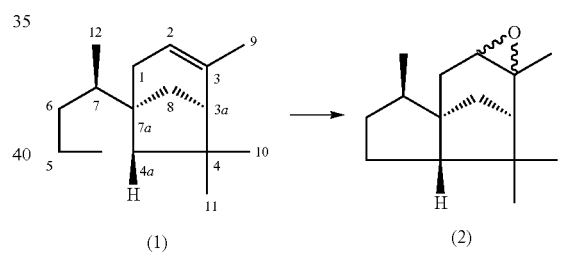

A mixture comprising the compound of formula (Ia) (as described hereinbefore) and the compound of formula (Ib) (as described hereinbefore) in a weight ratio of 90:10 to 99:1 is disclosed in the patent application EP 2 947 078 A1. Such a mixture may be provided in essentially crystalline form.

Depending on the reaction conditions selected, Ambrocenide® is present as a particular diastereomeric mixture, i.e. as a mixture containing two, three or all of the compounds of formula (Ia), (Ib), (Ic) and (Id) (see above structural formulae).

One object of the present invention was the optimization of Ambrocenide® and the provision of mixtures which are preferably particularly strongly olfactorily active, i.e. of such mixtures which are capable of particularly effectively imparting and/or enhancing pleasant odour properties or of particularly effectively masking and/or reducing unpleasant odour impressions.

The above object is solved according to a first aspect of the present invention by a mixture comprising the compound of formula (Ia),

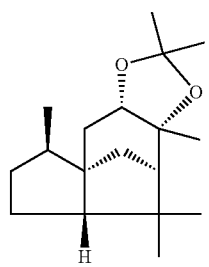
(Ia)

wherein the mixture is free or essentially free of the compound of formula (Ib), preferably of the compounds of formulae (Ib) and furthermore (Ic) and/or (Id)

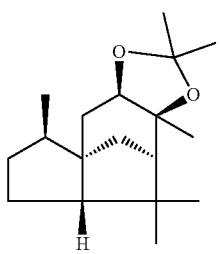
(Ib)

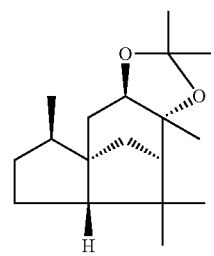
(Ic)

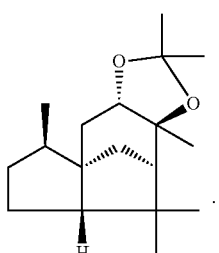
(Id)

The term "essentially free of the compound of formula (Ib), preferably of the compounds of formulae (Ib) and furthermore (Ic) and/or (Id)" is understood, in accordance with the present invention, to mean that the mixture according to the invention contains less than 1% by weight, preferably less than 0.1% by weight, particularly preferably less than 0.01% by weight, relative to the total weight of the mixture, of the compound of formula (Ib), preferably of the compounds of formulae (Ib) and furthermore (Ic) and/or (Id).

Surprisingly, in the context of the studies underlying the present invention, it was found that the compound of formula (Ia), as described herein, is much more olfactorily active than the compounds of formula (Ib), (Ic) and (Id). The compound of formula (Ia) is therefore particularly responsible for the odour properties of Ambrocenide®. It was previously unknown which of the stereoisomers of Ambrocenide® had which odour properties.

The mixture according to the invention therefore has particularly advantageous odour properties. In particular, it is possible to achieve the same or improved effects with a lower concentration of mixture according to the invention in comparison to the diastereomeric mixtures of Ambrocenide® known in the state of the art in terms of enhancing or imparting a pleasant odour impression and/or masking or reducing an unpleasant odour impression.

An advantage of the mixture according to the invention is therefore also its high odour intensity at a comparatively low dosage. This is of particular interest for reasons of environmental cleanliness, as the amount of substances released into the environment can be kept to a minimum.

Furthermore, according to a preferred embodiment, the present invention relates to a mixture as described herein, additionally containing one or several compound(s) of formula (II)

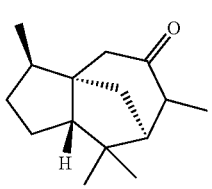
(II)

and/or of formula (III)

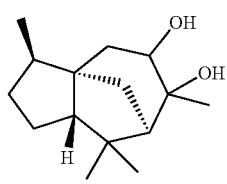
(III)

and/or of formula (IV)

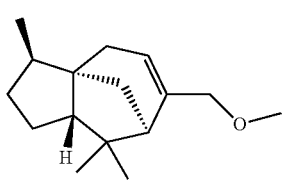
(IV)

and/or of formula (V)

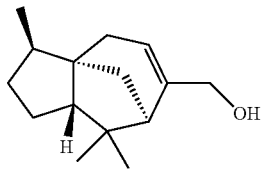

(V) and/or of formula (VI)

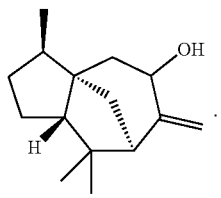

In particular, the presence of compound(s) of formula (II) (cedralone) in the mixture according to the invention is particularly advantageous as it enhances the top note and makes the scent of Ambrocenide® appear more animalistic.

Thereby, a mixture as described herein is particularly preferred, wherein the mixture contains one or several compound(s) of formula (II),

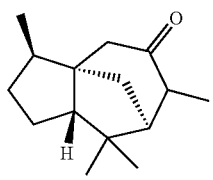

wherein the weight ratio of the total amount of compound of formula (Ia) to the total amount of compound(s) of formula (II) in the mixture is 500:1 to 3:1, preferably 350:1 to 5:1, particularly preferably 300:1 to 8:1, and/or wherein the mixture contains one or several compound(s) of formula (III),

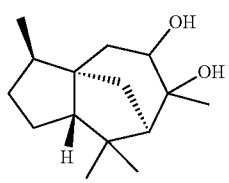

wherein the weight ratio of the total amount of compound of formula (Ia) to the total amount of compound(s) of formula (III) in the mixture is at least 5:1, preferably at least 10:1, particularly preferably at least 15:1, and/or wherein the mixture contains one or several compound(s) of formula (IV),

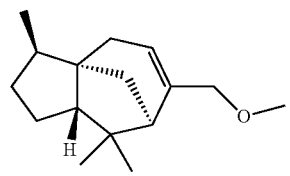

wherein the weight ratio of the total amount of compound of formula (Ia) to the total amount of compound(s) of formula (IV) in the mixture is at least 40:1, preferably at least 50:1, particularly preferably at least 60:1, and/or wherein the mixture contains one or several compound(s) of formula (V),

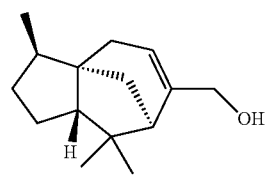

wherein the weight ratio of the total amount of compound of formula (Ia) to the total amount of compound(s) of formula (V) in the mixture is at least 30:1, preferably at least 40:1, more preferably at least 50:1, and/or wherein the mixture contains one or several compound(s) of formula (VI),

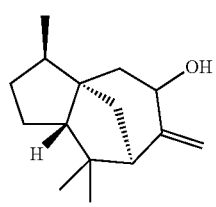

wherein the weight ratio of the total amount of compound of formula (Ia) to the total amount of compound(s) of formula (VI) in the mixture is at least 4:1, preferably at least 6:1, particularly preferably at least 8:1.

Particularly preferred thereby is an embodiment of the mixture according to the invention, wherein the mixture contains one or several compound(s) of formula (II) as described herein, and does not contain any compound(s) of formula (III) to (VI) as described herein.

Particularly preferred is an embodiment of the mixture according to the invention, wherein the mixture contains a compound of formula (II) as described herein, and does not contain any compound(s) of formula (III) to (VI) as described herein, and wherein the weight ratio of the total amount of compound of formula (Ia) to the total amount of compound(s) of formula (II) in the mixture is 500:1 to 3:1, preferably 350:1 to 5:1, more preferably 300:1 to 8:1, particularly preferably 280:1 to 260:1.

Furthermore, an alternative embodiment of the mixture according to the invention is preferred, wherein the mixture contains at least one or several compound(s) of formula (II), (111), (IV), (V) and (VI) as described herein, respectively. Particularly preferred thereby is such an alternative embodiment of the mixture according to the invention, wherein the mixture contains at least one or several compound(s) of formula (II), (III), (IV), (V) and (VI) as described herein, respectively, and wherein the weight ratio of the total amount of compound of the formula (Ia) to the total amount of compound(s) of formula (II) in the mixture is 500:1 to 3:1, preferably 350:1 to 5:1, more preferably 300:1 to 8:1, particularly preferably 12:1 to 8:1.

A further aspect of the present invention relates to a method for manufacturing a mixture as described herein, consisting of or comprising the following steps:

a) Providing a starting mixture, containing or consisting essentially of alpha,alpha-cedranediol of formula (IIIa),

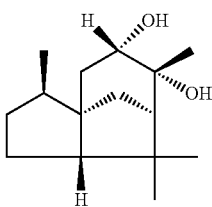

(IIIa)

wherein the starting mixture is free or essentially free of beta,beta-cedranediol of formula (IIIb),

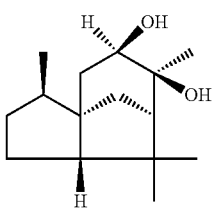

(IIIb)

preferably wherein the starting mixture is free or essentially free of beta,beta-cedranediol of the formula (IIIb) and furthermore of beta,alpha-cedranediol of the formula (IIIc) and/or alpha,beta-cedranediol of the formula (IIId),

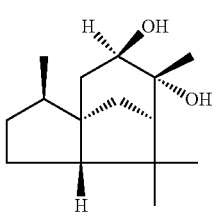

(IIIc)

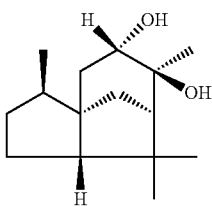

(IIId)

or providing the compound alpha,alpha-cedranediol of formula (IIIa),

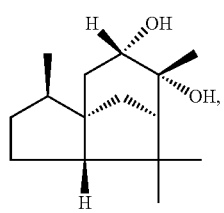

(IIIa)

b) reacting the starting mixture or compound from step a) with dimethoxypropane, wherein the method preferably furthermore comprises the following step:

c) Crystallizing the reaction product from step b) from aqueous alcoholic solution.

The term "consisting essentially of alpha,alpha-cedranediol of formula (IIIa)" in step a) of the method is understood, in accordance with the present invention, to mean that the starting mixture according to the invention contains at least 95% by weight, preferably at least 98% by weight, particularly preferably at least 99% by weight, particularly preferably at least 99.9% by weight, more preferably at least 99.99% by weight, based on the total weight of the starting mixture, of alpha,alpha-cedranediol of formula (IIIa).

The term "essentially free of beta,beta-cedranediol of formula (IIIb), preferably essentially free of beta,beta-cedranediol of formula (IIIb) and furthermore of beta,alpha-cedranediol of formula (IIIc) and/or alpha,beta-cedranediol of the formula (IIId)" is understood, in accordance with the present invention, to mean that the starting mixture according to the invention contains less than 1% by weight, preferably less than 0.1% by weight, particularly preferably less than 0.01% by weight, based on the total weight of the starting mixture, of beta,beta-cedranediol of formula (IIIb), preferably of beta,beta-cedranediol of the formula (IIIb) and furthermore of beta,alpha-cedranediol of formula (IIIc) and/or alpha,beta-cedranediol of the formula (IIId).

With respect to the above-mentioned step b) of the method according to the invention, a reaction of the starting mixture or the compound from step a) with dimethoxypropane in a molar ratio in the range of from about 1:5 to about 1:1, in particular from about 1:3, with respect to the total molar amount of compounds of the formula (III) to the total molar amount of dimethoxypropane is preferred.

Another aspect of the present invention relates a mixture as described herein, producible by a method as described herein.

The above definitions and (preferred) embodiments of the method according to the invention are thereby applicable accordingly and lead to particularly preferred embodiments of the mixture according to the invention.

In a further aspect, the present invention relates to a fragrance substance composition, preferably perfume oil, containing or consisting of a mixture according to the invention as described herein and preferably furthermore one or several additional fragrance substances, preferably wherein the additional or one, several or all of the additional fragrance substances is or are selected from the group consisting of 3-(4-methyl-1-cyclohex-3-enyl)-butanal, 4-(4-hydroxyphenyl) butan-2-one, (E)-4-(2,6,6-trimethyl-1-cyclohex-2-enyl)but-3-en-2-one, (E)-4-(2,6,6-trimethyl-1-cyclohex-2-enyl)but-3-en-2-one, (E)-1-(2,6,6-trimethyl-cyclohexen-1-yl)pent-1-en-3-one, (E)-4-[(1S)-1,2,6,6-tetramethylcyclohex-2-en-1-yl]-but-3-en-2-one, 1-(2,6,6-trimethyl-1-cyclohex-2-enyl)pent-1-en-3-one, [(Z)-hex-3- enyl]methyl carbonate, 3-[(Z)-hex-3-enoxy]propanenitrile, 1-(2,3,8,8-tetramethyl-1,3,4,5,6,7-hexa-hydronaphthalene-2-yl)ethanone, spiro[1,3-dioxolan-2,5'-(4',4',8',8'-tetramethyl-hexahydro-3',9'-methanonaphthalene)], [3R-(3α,3aβ, 6β,7β,8aα)]-octa-hydro-6-methoxy-3,6,8,8-tetramethyl-1H-3a,7-methanoazulene, [3R-(3α,3aβ,7β,8aα)]-1-(2,3,4,7, 8,8a-hexahydro-3,6,8,8-tetramethyl-1H-3a,7-methano-azulen-5-yl)ethan-1-one, 1-(2,2,6-trimethyl-cyclohexyl) hexan-3-ol, 6,6-dimethoxy-2,5,5-trimethylhex-2-ene, 2,6-dimethyloct-7-en-2-ol, 3,7-dimethylocta-1,6-dien-3-ol, (3,7-dimethylocta-1,6-dien-3-yl)acetate, (4-methyl-1-propan-2-yl-1-cyclohex-2-enyl)acetate, (8E)-cyclohexadec-8-en-1-one, 16-oxacyclohexa-decan-1-one, 1,3,4,6,7,8-hexahydro-4,6,6,7,8,8-hexamethyl-cyclopenta(g)-2-benzopyran, ethoxymethoxycyclo-dodecane, 1,1,2,3,3-pentamethyl-2,5, 6,7-tetrahydroinden-4-one, 1-(2,3,8,8-tetramethyl-1,3,4,5,6, 7-hexa-hydronaphthalene-2-yl)ethanone.

Similarly, according to another preferred embodiment, the present invention also relates to a fragrance substance composition as described herein, wherein the amount of mixture according to the invention as described herein or the amount of compound of formula (Ia) is sufficient,

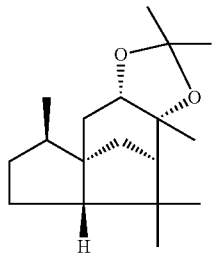

(Ia)

(a) to mask or to reduce the or one or several unpleasant odour impressions of another fragrance substance in the fragrance substance composition,
and/or
(b) to enhance the or one or several pleasant odour impressions of another fragrance substance in the fragrance substance composition.

Preferred is further a fragrance substance composition according to the invention, preferably perfume oil, as described herein, wherein the total amount of compound of formula (Ia)

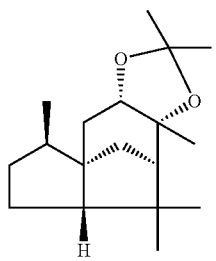

(Ia)

is 0.01 to 10% by weight, preferably 0.03 to 5% by weight, particularly preferably 0.05 to 2% by weight, based on the total weight of the fragrance substance composition.

In a further aspect, the present invention relates to a perfumed product, containing a mixture according to the invention as described herein or preferably a fragrance substance composition according to the invention, preferably a perfume oil, as described herein in a sensorially effective amount, wherein the proportion of the mixture or the fragrance substance composition, based on the total weight of the product, is preferably in the range of from 0.01 to 10% by weight, preferably 0.1 to 5% by weight, particularly preferably 0.25 to 3% by weight.

According to a preferred embodiment, the perfumed product according to the invention as described herein is selected from the group consisting of perfume extracts, eau de parfums, eau de toilettes, aftershaves, eau de colognes, pre-shave products, splash colognes, perfumed refreshing wipes, acidic, alkaline and neutral detergents, textile fresheners, ironing aids, liquid detergents, powdery detergents, laundry pre-treatment agents, fabric softeners, washing soaps, washing tablets, disinfectants, surface disinfectants, air fresheners, aerosol sprays, waxes and polishes, body care products, hand creams and lotions, foot creams and lotions, depilatory creams and lotions, after-shave creams and lotions, tanning creams and lotions, hair care products, deodorants and antiperspirants, decorative cosmetic products, candles, lamp oils, incense sticks, insecticides, repellents and fuels.

In a further aspect, the present invention also relates to a method for manufacturing a perfumed product, preferably a product as described herein, comprising the following steps:
i) Providing a mixture according to the invention as described herein or a fragrance substance composition according to the invention as described herein,
ii) providing one or several further components of the perfumed product to be manufactured, and
iii) contacting or mixing the further components provided in step ii) with a sensorially effective amount of the components provided in step i).

In a further aspect, the present invention relates to the use of a mixture according to the invention as described herein or of a fragrance substance composition according to the invention as described herein
(a) for masking or reducing the or one or several unpleasant odour impressions of one or several unpleasantly smelling substances,
and/or
(b) for enhancing the or one or several pleasant odour impressions of one or several pleasantly smelling substances.

According to a preferred embodiment, the present invention relates to a use as described herein in a composition containing one or several (further) pleasantly and/or unpleasantly smelling substances, whose unpleasant odour impression is masked or reduced by a mixture according to the invention as described herein or a fragrance substance composition according to the invention as described herein and/or whose pleasant odour impression is enhanced by a mixture according to the invention as described herein or a fragrance substance composition according to the invention as described herein, preferably wherein this/these pleasantly and/or unpleasantly smelling substance or one, several or all of these pleasantly and/or unpleasantly smelling substances is or are selected from the group consisting of 3-(4-methyl-1-cyclohex-3-enyl)-butanal, 4-(4-hydroxyphenyl) butan-2-one, (E)-4-(2,6,6-trimethyl-1-cyclohex-2-enyl)but-3-en-2-one, (E)-4-(2,6,6-trimethyl-1-cyclohex-2-enyl)but-3-en-2-one, (E)-1-(2,6,6-trimethyl-cyclohexen-1-yl)pent-1-en-3-one, (E)-4-[(1 S)-1,2,6,6-tetramethylcyclohex-2-en-1-yl]-but-3-en-2-one, 1-(2,6,6-trimethyl-1-cyclohex-2-enyl)pent-1-en-3-one, [(Z)-hex-3-enyl]methyl carbonate, 3-[(Z)-hex-3-enoxy]propanenitrile, 1-(2,3,8,8-tetramethyl-1,3,4,5,6,7- hexa-hydronaphthalene-2-yl)ethanone, spiro[1,3-dioxolan-2,5'-(4',4',8',8'-tetramethyl-hexahydro-3',9'-methano-naphthalene)], [3R-(3α,3aβ,6β,7β,8aα)]-octa-hydro-6-methoxy-3,6,8,8-tetramethyl-1H-3a,7-methanoazulene,[3R-(3α,3aβ,7β,8aα)]-1-(2,3,4,7,8,8a-hexa-hydro-3,6,8,8-tetramethyl-1H-3a,7-methano-azulen-5-yl)ethan-1-one, 1-(2,2,6-trimethyl-cyclohexyl)hexan-3-ol, 6,6-dimethoxy-2,5,5-trimethylhex-2-ene, 2,6-dimethyloct-7-en-2-ol, 3,7-dimethylocta-1,6-dien-3-ol, (3,7-dimethylocta-1,6-dien-3-yl)acetate, (4-methyl-1-propan-2-yl-1-cyclohex-2-enyl) acetate, (8E)-cyclohexadec-8-en-1-one, 16-oxacyclohexadecan-1-one, 1,3,4,6,7,8-hexahydro-4,6,6,7,8,8-hexamethyl-cyclopenta(g)-2-benzopyran, ethoxymethoxy-cyclododecane, 1,1,2,3,3-pentamethyl-2,5,6,7-tetrahydroinden-4-one, 1-(2,3,8,8-tetramethyl-1,3,4,5,6,7-hexa-hydronaphthalene-2-yl)ethanone.

Preferred according to the invention is a use as described herein, for enhancing the or one or several odour impressions selected from the group consisting of the odour notes floral, preferably lily of the valley, amber, woody, musk, violet, citrus and aldehyde.

According to a further aspect, the present invention relates to a method
(a) for masking or reducing the or one or several unpleasant odour impressions of one or several unpleasantly smelling substances,
and/or
(b) for enhancing the or one or several pleasant odour impressions of one or several pleasantly smelling substances,
comprising the following step:

Mixing the (a) pleasantly and/or (b) unpleasantly smelling substances with a mixture according to the invention as described herein or a fragrance substance composition according to the invention as described herein,
wherein the amount of mixture according to the invention as described herein or of fragrance substance composition according to the invention as described herein is sufficient to (a) enhance the pleasant odour impression(s) of the pleasantly smelling substance(s) and/or (b) to reduce or to mask the unpleasant odour impression(s) of the unpleasantly smelling substance(s).

For the aspects according to the invention as described above what has been stated above in connection with a mixture according to the invention preferably applies accordingly, respectively, and also what has been stated in connection with the aspects according to the invention as described above applies accordingly to the mixture according to the invention. Moreover, the embodiments described herein can be arbitrarily combined with each other as long as it makes technical sense.

This invention is explained in more detail using the following examples. Unless otherwise stated, all specifications refer to the weight.

Example 1: Preparation of a Mixture According to Invention 70 kg of dimethoxypropane (95%) in 62 kg of acetone are placed in a stirring vessel and 50 kg of a starting mixture are added consisting of 99% by weight of alpha,alpha-cedranediol of formula (IIIa) as described herein, the starting mixture being free of beta,beta-cedranediol of formula (IIIb), beta,alpha-cedranediol of formula (IIIc) and alpha,beta-cedranediol of formula (IIId) as described herein. A solution consisting of 53 kg of acetone and 0.167 kg of technical sulphuric acid is then added at a temperature of not more than 30° C. for a period of 2 hours. After a further stirring time of 4 hours, the reaction mixture is adjusted to a pH of at least 8 with a slurry consisting of 1.6 kg of calcined soda in 5 kg of water.

During subsequent distillation, the low boilers are removed from the reaction mixture to such an extent that a sump temperature of 95° C. is not exceeded. When the distillation is complete, 38 kg of methyl-tert.-butyl ether are added to the distillation residue and stirred at a temperature of about 35° C. for about 30 minutes. The reaction mixture is then left to rest until a clear two-phase mixture is obtained. The aqueous phase is separated off and 12 kg of water are added to the remaining organic phase. The mixture obtained is stirred at a temperature of about 35° C. for about 30 minutes. The reaction mixture is then left to rest until a clear two-phase mixture is obtained. The aqueous phase is separated off and methyl-tert.-butyl ether is removed during subsequent distillation of the organic phase to such an extent that a sump temperature of 95° C. is not exceeded at 40 mbar. The distillation residue is taken up in 100 kg of heptane and recrystallized with an aqueous ethanolic solution.

The reaction product obtained is a mixture according to the invention, consisting of 95% by weight of the compound of formula (Ia) as described herein, the mixture being free of compounds of formula (Ib), (Ic) and (Id) as described herein.

Comparative Example 1: Manufacture of a Mixture Consisting Essentially of a Compound of Formula (Ia) and a Compound of Formula (Ib)

60 kg of dimethoxypropane (95%) in 62 kg of acetone are placed in a stirring vessel and 50 kg of a mixture of isomers, 85% by weight of which consists of compounds of formula (III) as described herein (essentially alpha,alpha-cedranediol of formula (IIIa) and beta,beta-cedranediol of formula (IIIb), wherein the weight ratio of the compound of formula (IIIa) to the compound of formula (IIIb) is in the range of from 95:5 to 99.9:0.1, and further beta,alpha-cedranediol (formula (IIIc)) and alpha,beta-cedranediol (formula (IIId)), are added. The isomer mixture may also contain up to 15% by weight, based on the total weight of the isomer mixture used, of compounds of the formula (II) and (IV) to (VI). A solution consisting of 53 kg acetone and 0.167 kg technical sulphuric acid is then added at a temperature of not more than 30° C. for a period of 2 hours. After a further stirring period of 4 hours, the reaction mixture is adjusted to a pH of at least 8 using a slurry consisting of 1.6 kg of calcined soda in 5 kg of water.

During subsequent distillation, the low boilers are removed from the reaction mixture to such an extent that a sump temperature of 95° C. is not exceeded. When the distillation is complete, 38 kg of methyl-tert.-butyl ether are added to the distillation residue and stirred at a temperature of about 35° C. for about 30 minutes. The reaction mixture is then left to rest until a clear two-phase mixture is obtained. The aqueous phase is separated off and 12 kg of water are added to the remaining organic phase. The mixture obtained is stirred at a temperature of about 35° C. for about 30 minutes. The reaction mixture is then left to rest until a clear two-phase mixture is obtained. The aqueous phase is separated off and methyl-tert.-butyl ether is removed during subsequent distillation of the organic phase to such an extent that a sump temperature of 95° C. is not exceeded at 40 mbar. The distillation residue is taken up in 100 kg of heptane and recrystallized with an aqueous ethanolic solution.

The reaction product obtained is a mixture not according to the invention consisting of a total of 83% by weight of compound of formula (Ia) and compound of formula (Ib) as described herein, the weight ratio of the compound of formula (Ia) to the compound of formula (Ib) in the mixture being 95:5.

Example 2: Parfume Oils

TABLE 1

Reaction product from comparative example 1 (VB) in the aldehyde environment using the example of the following accord:

| Components | A (VB) | B (VB) | C (VB) | D (VB) | E (VB) | F (VB) |
|---|---|---|---|---|---|---|
| Aldehyde C11 MOA 10% 2-Methyldecanal | 285.00 | 285.00 | 285.00 | 285.00 | 285.00 | 285.00 |
| Aldehyde C11 10% Undecanal | 95.00 | 95.00 | 95.00 | 95.00 | 95.00 | 95.00 |
| Aldehyde C12 MNA 10% 2-Methylundecanal | 38.00 | 38.00 | 38.00 | 38.00 | 38.00 | 38.00 |
| Farenal ® 10% 2,6,10-Trimethyl-undec-9-enal | 76.00 | 76.00 | 76.00 | 76.00 | 76.00 | 76.00 |
| Florazon 10% 3-(4-Ethylphenyl)-2,2-dimethylpropanal | 209.00 | 209.00 | 209.00 | 209.00 | 209.00 | 209.00 |
| Limonenal 10% 3-(4-Methyl-1-cyclohex-3-enyl)-butanal | 95.00 | 95.00 | 95.00 | 95.00 | 95.00 | 95.00 |
| Mandarin Aldehyde 10% TEC (E)-Dodec-2-enal | 114.00 | 114.00 | 114.00 | 114.00 | 114.00 | 114.00 |
| Ozonil 10% Tridec-2-enenitrile | 38.00 | 38.00 | 38.00 | 38.00 | 38.00 | 38.00 |
| Reaction product from comparative example 1 | — | 0.50 | 1.00 | 5.00 | 10.00 | 30.00 |
| DPG | 50.00 | 49.50 | 49.00 | 45.00 | 40.00 | 20.00 |
| Sum | 1000.00 | 1000.00 | 1000.00 | 1000.00 | 1000.00 | 1000.00 |

TABLE 2

Reaction product from example 1 (B) in the aldehyde environment using the example of the following accord:

| Components | A (B) | B (B) | C (B) | D (B) | E (B) | F (B) |
|---|---|---|---|---|---|---|
| Aldehyde C11 MOA 10% 2-Methyldecanal | 285.00 | 285.00 | 285.00 | 285.00 | 285.00 | 285.00 |
| Aldehyde C11 10% Undecanal | 95.00 | 95.00 | 95.00 | 95.00 | 95.00 | 95.00 |
| Aldehyde C12 MNA 10% 2-Methylundecanal | 38.00 | 38.00 | 38.00 | 38.00 | 38.00 | 38.00 |
| Farenal ® 10% 2,6,10-Trimethyl-undec-9-enal | 76.00 | 76.00 | 76.00 | 76.00 | 76.00 | 76.00 |
| Florazon 10% 3-(4-Ethylphenyl)-2,2-dimethylpropanal | 209.00 | 209.00 | 209.00 | 209.00 | 209.00 | 209.00 |
| Limonenal 10% 3-(4-Methyl-1-cyclohex-3-enyl)-butanal | 95.00 | 95.00 | 95.00 | 95.00 | 95.00 | 95.00 |
| Mandarin Aldehyde 10% TEC (E)-Dodec-2-enal | 114.00 | 114.00 | 114.00 | 114.00 | 114.00 | 114.00 |
| Ozonil 10% Tridec-2-enenitrile | 38.00 | 38.00 | 38.00 | 38.00 | 38.00 | 38.00 |
| Reaction product from example 1 | — | 0.50 | 1.00 | 5.00 | 10.00 | 30.00 |
| DPG | 50.00 | 49.50 | 49.00 | 45.00 | 40.00 | 20.00 |
| Sum | 1000.00 | 1000.00 | 1000.00 | 1000.00 | 1000.00 | 1000.00 |

In small doses, such as in B (VB) and C (VB), a stronger and more radiant development of the scent than in A (VB) can be observed when the reaction product from comparative example 1 is added. In C (VB) and D (VB), the addition of the reaction product from comparative example 1 also highlights the typical aldehyde, greasy and metallic character of the accord. In E (VB) and F (VB), the influence of the reaction product from comparative example 1 dominates and gives the accord a strongly ambery odour (for the composition of A (VB) to F (VB) see Table 1).

In comparison, the addition of the same amount of reaction product from example 1 instead of the addition of the reaction product from comparative example 1 in B (B) to F (B) surprisingly leads to an unexpected enhancement of the corresponding effects described for B (VB) to F (VB). In particular, in D (B) the influence of the reaction product from example 1 already dominates and gives the accord a strongly ambery odour. Furthermore, the perfume oils mixed with the reaction product from example 1 appear more radiant and ambery, whereby these effects can already be perceived in the dosage C (B) (for the composition of A (B) to F (B) see Table 2).

When using the mixtures according to the invention, lower concentrations can therefore be used to achieve the same effects.

Example 3: Perfumed Products

Washing Powder:

| Component | weight proportions | | |
|---|---|---|---|
| | (1) | (2) | (3) |
| Aldehyde C11 Undecylic 10% | 16.00 | 16.00 | 16.00 |
| Aldehyde C11 Undecylenic 10% | 18.00 | 18.00 | 18.00 |
| Aldehyde C12 Lauric 10% | 14.00 | 14.00 | 14.00 |
| Aldehyde C12 MNA 10% | 12.00 | 12.00 | 12.00 |
| Hexenal Trans-2 10% | 4.00 | 4.00 | 4.00 |
| Hexenyl Acetate Cis-3 | 4.00 | 4.00 | 4.00 |
| Vertocitral | 10.00 | 10.00 | 10.00 |
| Magnolan | 130.00 | 130.00 | 130.00 |
| Mintonat | 35.00 | 35.00 | 35.00 |
| Dihydro Myrcenol | 70.00 | 70.00 | 70.00 |
| Orange Oil | 35.00 | 35.00 | 35.00 |
| Nerolione 10% | 3.50 | 3.50 | 3.50 |
| Cantryl ® | 3.50 | 3.50 | 3.50 |
| Hexyl Acetate | 18.00 | 18.00 | 18.00 |
| Jasmaprunat | 18.00 | 18.00 | 18.00 |
| Aldehyde C14 So-Called | 50.00 | 50.00 | 50.00 |
| Ethyl Methyl Butyrate-2 | 8.00 | 8.00 | 8.00 |
| Manzanate | 1.20 | 1.20 | 1.20 |
| Allyl Cyclohexyl Propionate | 8.00 | 8.00 | 8.00 |
| Aprifloren ® | 3.00 | 3.00 | 3.00 |
| Fruitate | 1.80 | 1.80 | 1.80 |
| Ethyl Linalool | 56.00 | 56.00 | 56.00 |
| Dimethyl Benzyl Carbinyl Butyrate | 7.00 | 7.00 | 7.00 |
| Rose Abs. Type Base | 30.00 | 30.00 | 30.00 |
| Rosaphen ® | 30.00 | 30.00 | 30.00 |
| Damascenone Total | 1.20 | 1.20 | 1.20 |
| Damascone Alpha | 1.80 | 1.80 | 1.80 |
| Benzyl Acetate | 28.00 | 28.00 | 28.00 |
| Hedione | 56.00 | 56.00 | 56.00 |
| Hexyl Cinnamic Aldehyde Alpha | 130.00 | 130.00 | 130.00 |
| Parmanyl ® | 3.50 | 3.50 | 3.50 |
| Isoraldeine 70 | 28.00 | 28.00 | 28.00 |
| Isoeugenyl Acetate | 3.50 | 3.50 | 3.50 |
| Agrumex HC | 50.00 | 50.00 | 50.00 |
| Ambroxide Cryst. | 1.50 | 1.50 | 1.50 |
| Reaction product from comparative example 1 | 0.80 | — | — |
| Reaction product from example 1 | — | 0.40 | 0.80 |
| Dipropylene Glycol | 109.70 | 110.10 | 109.70 |
| Sum | 1000.00 | 1000.00 | 1000.00 |

The reaction product from comparative example 1 (column (1)) underlines the warm woody base note and supports adhesion on the laundry. In comparison, the same effect can be achieved with only half the concentration of the reaction product from example 1 compared to the reaction product from comparative example 1 (column (2)). If the same amount of reaction product from example 1 is used as the reaction product from comparative example 1 (column (3)), the odour note appears more radiant, ambery and of higher quality than that of the product described in column (1).

Shampoo:

| Component | weight proportions | | |
|---|---|---|---|
| | (1) | (2) | (3) |
| Hexenol Cis-3 | 2.50 | 2.50 | 2.50 |
| Galbanum Oil 10% | 5.00 | 5.00 | 5.00 |
| Magnolan | 25.00 | 25.00 | 25.00 |
| Bergamot Oil RCO | 80.00 | 80.00 | 80.00 |
| Linalyl Acetate | 120.00 | 120.00 | 120.00 |
| Lemon Oil | 80.00 | 80.00 | 80.00 |
| Neroli Base | 10.00 | 10.00 | 10.00 |
| Lavender Oil | 6.00 | 6.00 | 6.00 |
| Thyme Oil 10% | 6.00 | 6.00 | 6.00 |
| Linalool | 60.00 | 60.00 | 60.00 |
| Phenylethyl Alcohol BA Free | 20.00 | 20.00 | 20.00 |
| Vitessence ® Rose De Mai | 6.50 | 6.50 | 6.50 |
| Narcisse Abs. 10% | 1.30 | 1.30 | 1.30 |
| Hedione | 80.00 | 80.00 | 80.00 |
| Jasmalactone Cis 10% | 6.00 | 6.00 | 6.00 |
| Parmanyl ® 10% | 12.70 | 12.70 | 12.70 |
| Ionone Beta | 6.00 | 6.00 | 6.00 |
| Methyl Ionone Gamma Pure | 18.00 | 18.00 | 18.00 |
| Irone Alpha 10% | 12.00 | 12.00 | 12.00 |
| Benzoin Siam Resin 50% | 5.00 | 5.00 | 5.00 |
| Coumarin | 5.00 | 5.00 | 5.00 |
| Iso E Super | 180.00 | 180.00 | 180.00 |
| Cashmeran | 12.00 | 12.00 | 12.00 |
| Isobutyl Quinoline 10% | 6.00 | 6.00 | 6.00 |
| Reaction product from comparative example 1 | 0.2 | — | — |
| Reaction product from example 1 | — | 0.1 | 0.2 |
| Globalide ® | 45.00 | 45.00 | 45.00 |
| Dipropylene Glycol | 189.80 | 189.90 | 189.80 |
| Sum | 1000.00 | 1000.00 | 1000.00 |

The reaction product from comparative example 1 (column (1)) enhances both the top note and the adhesive woody elements in the base note. In comparison, the same effect can be achieved with only half the concentration of the reaction product from example 1 compared to the reaction product from comparative example 1 (column (2)). If the same amount of reaction product from example 1 is used as the reaction product from comparative example 1 (column (3)), the odour note appears more ambery, nourishing and cosmetic than that of the product described in column (1).

The invention claimed is:

1. A mixture comprising a compound of formula (Ia),

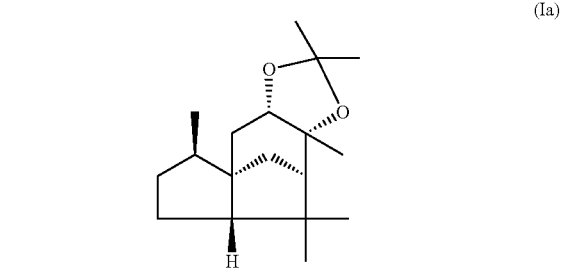 [SMILES: C[C@@H]1CC[C@H]2C(C)(C)[C@H]3C[C@@]12C[C@@H]1OC(C)(C)O[C@@]13C]

(Ia)

wherein the mixture is free of compounds of formulae (Ib), (Ic), and (Id)

(Ib)
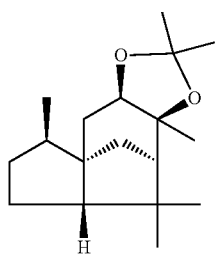

(Ic)
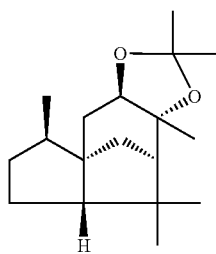

(Id)
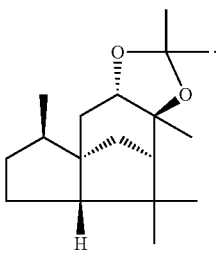

2. The mixture according to claim 1 further comprising one or more compound(s) of formula (II)

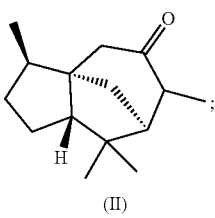
(II)

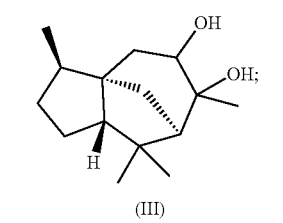
(III)

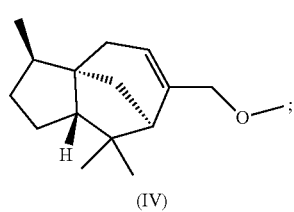
(IV)

formula (VI)
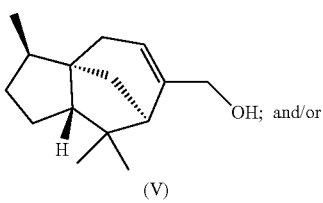
OH; and/or (V)

(VI)
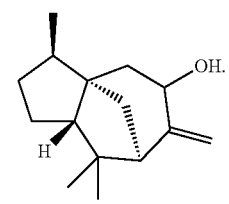
OH.

3. A mixture according to claim 1 further comprising:
one or more compound(s) of formula (II), (II)
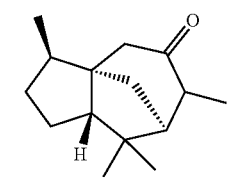

wherein a weight ratio of a total amount of the compound of formula (Ia) to a total amount of the compound(s) of formula (II) is 500:1 to 3:1;
one or more compound(s) of formula (III), (III)
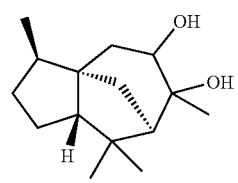

wherein a weight ratio of a total amount of the compound of formula (Ia) to a total amount of the compound(s) of formula (III) is at least 5:1;
one or more compound(s) of formula (IV), (IV)
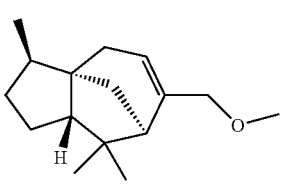

wherein a weight ratio of a total amount of the compound of formula (Ia) to a total amount of the compound(s) of formula (IV) is at least 40:1;

one or more compound(s) of formula (V),

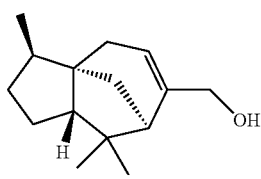
(V)

wherein a weight ratio of a total amount of the compound of formula (Ia) to a total amount of the compound(s) of formula (V) is at least 30:1; or and/or one or more compound(s) of formula (VI),

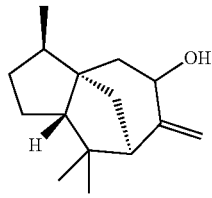
(VI)

wherein a weight ratio of the total amount of the compound of formula (Ia) to the total amount of the compound(s) of formula (VI) is at least 4:1.

4. A fragrance substance composition comprising:
a mixture according to claim 1; and
one or more compounds selected from 3-(4-methyl-1-cyclohex-3-enyl)-butanal, 4-(4-hydroxyphenyl) butan-2-one, (E)-4-(2,6,6-trimethyl-1-cyclohex-2-enyl)but-3-en-2-one, (E)-4-(2,6,6-trimethyl-1-cyclohex-2-enyl) but-3-en-2-one, (E)-1-(2,6,6-trimethyl-cyclohexen-1-yl)pent-1-en-3-one, (E)-4-[(1S)-1,2,6,6-tetramethylcyclohex-2-en-1-yl]-but-3-en-2-one, 1-(2,6,6-trimethyl-1-cyclohex-2-enyl)pent-1-en-3-one, [(Z)-hex-3-enyl] methyl carbonate, 3-[(Z)-hex-3-enoxy] propanenitrile, 1-(2,3,8,8-tetramethyl-1,3,4,5,6,7-hexahydronaphthalene-2-yl)ethanone, spiro[1,3-dioxolan-2,5'-(4',4',8',8'-tetramethyl-hexahydro-3',9'-methanonaphthalene)], [3R-(3α,3aβ,6β,7β,8aα)]-octahydro-6-methoxy-3,6,8,8-tetramethyl-1H-3a,7-methanoazulene, [3R-(3α,3aβ,6β,7β,8aα)]-1-(2,3,4,7,8,8a-hexahydro-3,6,8,8-tetramethyl-1H-3a,7-methanoazulen-5-yl)ethan-1-one, 1-(2,2,6-trimethyl-cyclohexyl) hexan-3-ol, 6,6-dimethoxy-2,5,5-trimethylhex-2-ene, 2,6-dimethyloct-7-en-2-ol, 3,7-dimethylocta-1,6-dien-3-ol, (3,7-dimethylocta-1,6-dien-3-yl)acetate, (4-methyl-1-propan-2-yl-1-cyclohex-2-enyl)acetate, (8E)-cyclohexadec-8-en-1-one, 16-oxacyclohexa-decan-1-one, 1,3,4,6,7,8-hexahydro-4,6,6,7,8,8-hexamethyl-cyclopenta(g)-2-benzopyran, ethoxymethoxycyclo-dodecane, 1,1,2,3,3-pentamethyl-2,5,6,7-tetrahydroinden-4-one, and 1-(2,3,8,8-tetramethyl-1,3,4,5,6,7-hexa-hydronaphthalene-2-yl)ethanone.

5. The fragrance substance composition according to claim 4, wherein an amount of the compound of formula (Ia) is sufficient:

(c) to mask or to reduce unpleasant odour impressions of another substance in the fragrance substance composition, and/or (d) to enhance pleasant odour impressions of another substance in the fragrance substance composition.

6. The fragrance substance composition according to claim 4, wherein the total amount of the compound of formula (Ia) is 0.01 to 10% by weight, based on the total weight of the fragrance substance composition.

7. The fragrance substance composition according to claim 6, wherein the total amount of the compound of formula (Ia) is 0.03 to 5% by weight, based on the total weight of the fragrance substance composition.

8. The fragrance substance composition according to claim 4, being a product selected from the group consisting of perfume extracts, eau de parfums, eau de toilettes, after-shaves, eau de colognes, pre-shave products, splash colognes, perfumed refreshing wipes, acidic, alkaline and neutral detergents, textile fresheners, ironing aids, liquid detergents, powdery detergents, laundry pre-treatment agents, fabric softeners, washing soaps, washing tablets, disinfectants, surface disinfectants, air fresheners, aerosol sprays, waxes and polishes, body care products, hand creams and lotions, foot creams and lotions, depilatory creams and lotions, after-shave creams and lotions, tanning creams and lotions, hair care products, deodorants and antiperspirants, decorative cosmetic products, candles, lamp oils, incense sticks, insecticides, repellents and fuels.

9. A method for manufacturing a mixture according to claim 1, comprising:
a) providing a feed mixture comprising alpha,alpha-cedranediol of formula (IIIa),

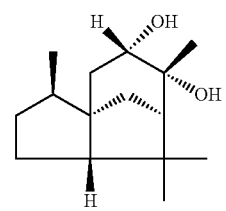
(IIIa)

wherein the feed mixture is free of beta,beta-cedranediol of formula (IIIb),

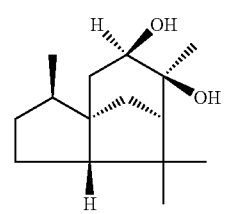
(IIIb)

b) reacting the alpha,alpha-cedranediol of formula (IIIa) with dimethoxypropane.

10. The method for manufacturing a mixture according to claim 9 further comprising:
c) crystallizing the reaction product from step b) from aqueous alcoholic solution.

11. A method for manufacturing a perfumed product comprising:
   i) providing a mixture according to claim 1;
   ii) providing one or more compounds selected from 3-(4-methyl-1-cyclohex-3-enyl)-butanal, 4-(4-hydroxyphenyl) butan-2-one, (E)-4-(2,6,6-trimethyl-1-cyclohex-2-enyl)but-3-en-2-one, (E)-4-(2,6,6-trimethyl-1-cyclohex-2-enyl)but-3-en-2-one, (E)-1-(2,6,6-trimethyl-cyclohexen-1-yl)pent-1-en-3-one, (E)-4-[(1S)-1,2,6,6-tetramethylcyclohex-2-en-1-yl]-but-3-en-2-one, 1-(2,6,6-trimethyl-1-cyclohex-2-enyl)pent-1-en-3-one, [(Z)-hex-3-enyl] methyl carbonate, 3-[(Z)-hex-3-enoxy]propanenitrile, 1-(2,3,8,8-tetramethyl-1,3,4,5,6,7-hexa-hydronaphthalene-2-yl)ethanone, spiro[1,3-dioxolan-2,5'-(4',4',8',8'-tetramethyl-hexahydro-3',9'-methanonaphthalene)], [3R-(3α,3aβ,6β,7β,8aα)]-octa-hydro-6-methoxy-3,6,8,8-tetramethyl-1H-3a,7-methanoazulene, [3R-(3α,3aβ,7β,8aα)]-1-(2,3,4,7,8,8a-hexahydro-3,6,8,8-tetramethyl-1H-3a,7-methano-azulen-5-yl)ethan-1-one, 1-(2,2,6-trimethyl-cyclohexyl) hexan-3-ol, 6,6-dimethoxy-2,5,5-trimethylhex-2-ene, 2,6-dimethyloct-7-en-2-ol, 3,7-dimethylocta-1,6-dien-3-ol, (3,7-dimethylocta-1,6-dien-3-yl)acetate, (4-methyl-1-propan-2-yl-1-cyclohex-2-enyl) acetate, (8E)-cyclohexadec-8-en-1-one, 16-oxacyclohexa-decan-1-one, 1,3,4,6,7,8-hexahydro-4,6,6,7,8,8-hexamethyl-cyclopenta(g)-2-benzopyran, ethoxymethoxycyclo-dodecane, 1,1,2,3,3-pentamethyl-2,5,6,7-tetrahydroinden-4-one, 1-(2,3,8,8-tetramethyl-1,3,4,5,6,7-hexa-hydronaphthalene-2-yl)ethanone, and
   iii) contacting or mixing the compound(s) provided in step ii) with a sensorially effective amount of the mixture provided in step i).

12. The method according to claim 11, wherein the amount of the mixture of i) is sufficient to (a) enhance a pleasant odour impression of a pleasantly smelling substance and/or (b) to reduce an unpleasant odour impression of an unpleasantly smelling substance.

* * * * *